United States Patent
Lin et al.

(10) Patent No.: US 10,973,755 B2
(45) Date of Patent: Apr. 13, 2021

(54) **METHOD FOR TREATING SKIN AGING AND PHOTODAMAGE BY USING *CAMELLIA SINENSIS* CALLUS EXTRACT**

(71) Applicant: TCI CO., LTD, Taipei (TW)

(72) Inventors: Yung-Hsiang Lin, Taipei (TW); Cheng-Shing Li, Taipei (TW)

(73) Assignee: TCI CO., LTD., Taipei (TW)

(*) Notice: Subject to any disclaimer, the term of this patent is extended or adjusted under 35 U.S.C. 154(b) by 54 days.

(21) Appl. No.: 15/918,979

(22) Filed: Mar. 12, 2018

(65) Prior Publication Data

US 2018/0256484 A1    Sep. 13, 2018

Related U.S. Application Data

(60) Provisional application No. 62/470,564, filed on Mar. 13, 2017.

(51) Int. Cl.
| | | |
|---|---|---|
| *A61K 8/96* | (2006.01) | |
| *A61K 36/82* | (2006.01) | |
| *A61P 17/02* | (2006.01) | |
| *A61P 17/16* | (2006.01) | |
| *A61Q 17/04* | (2006.01) | |
| *A61Q 19/08* | (2006.01) | |
| *A61K 8/9789* | (2017.01) | |

(52) U.S. Cl.
CPC .............. *A61K 8/96* (2013.01); *A61K 8/9789* (2017.08); *A61K 36/82* (2013.01); *A61P 17/02* (2018.01); *A61P 17/16* (2018.01); *A61Q 19/08* (2013.01); *A61Q 17/04* (2013.01)

(58) Field of Classification Search
CPC ..................................................... A61K 36/82
See application file for complete search history.

(56) References Cited

U.S. PATENT DOCUMENTS

| | | | |
|---|---|---|---|
| 9,089,504 B2 | 7/2015 | Kang et al. | |
| 2010/0119463 A1* | 5/2010 | Jacobs | A61K 8/042 |
| | | | 424/59 |
| 2010/0136636 A1* | 6/2010 | Takemoto | C12N 5/04 |
| | | | 435/125 |
| 2014/0186315 A1* | 7/2014 | Kang | A61Q 19/08 |
| | | | 424/93.7 |
| 2015/0335611 A1 | 11/2015 | Niwano et al. | |

FOREIGN PATENT DOCUMENTS

| | | |
|---|---|---|
| CN | 103040674 A | 4/2013 |
| CN | 103889397 A | 6/2014 |
| CN | 104936587 A | 9/2015 |
| CN | 104983638 A | 10/2015 |
| CN | 105816507 A | 8/2016 |
| KR | 10-2011-0031801 A | 3/2011 |
| KR | 10-2013-0022471 A | 3/2013 |
| KR | 10-2014-0033957 A | 3/2014 |
| WO | WO 2016/166047 A1 | 10/2016 |

OTHER PUBLICATIONS

Sigma. Murashige and Skoog Basal Salt Mixture MS. Retreived 2020. (Year: 2020).*
Yoriyuki Nakamura. In Vitro Propagation Tecniques of Tea Plants. (Year: 1991).*
CDC. Necrotizing Fascititis: All you need to Know. Retreived 2020. (Year: 2020).*
"Theory of Callus Induction and Culture," https://blog.naver.com/tsung15/220261912945 6 pages (Feb. 3, 2015).
"Cosmetic Ingredient," BIO-FD&C, 6 pages (Feb. 1, 2017).

* cited by examiner

*Primary Examiner* — Sarah Alawadi
(74) *Attorney, Agent, or Firm* — Christensen, Fonder, Dardi & Herbert PLLC

(57) ABSTRACT

A method for protecting skin is provided. The method comprises administering to a subject in need a composition, wherein the composition comprises an effective amount of a *Camellia sinensis* callus extract, and the extract is a polar solvent extract of calluses of *Camellia sinensis* leaves. The method is especially for nursing skin, repairing skin, improving skin condition, delaying skin aging, assisting in maintaining content of collagen in skin, against photodamage, preventing skin lesions, and/or promoting wound healing.

12 Claims, 3 Drawing Sheets

Control group　　　　UVA　　　　UVA + extract

METHOD FOR TREATING SKIN AGING AND PHOTODAMAGE BY USING *CAMELLIA SINENSIS* CALLUS EXTRACT

CROSS REFERENCE TO RELATED APPLICATIONS

This application claims priority to U.S. Provisional Application Ser. No. 62/470,564 filed on Mar. 13, 2017, in the United States Patent and Trademark Office, the disclosures of which are incorporated herein in their entirety by reference.

FIELD OF THE INVENTION

The present invention relates to the uses of a *Camellia sinensis* callus extract in protecting skin, particularly to the uses of an extract of calluses of *Camellia sinensis* leaves in protecting skin. The protecting skin uses include nursing skin, repairing skin, improving skin condition, delaying skin aging, assisting in maintaining content of collagen in skin, against photodamage, preventing skin lesions, and/or promoting wound healing.

BACKGROUND OF THE INVENTION

Collagen, which is mainly distributed in the extracellular matrix and connective tissues, is the primary structural protein in animal body and is capable of supporting the structure of cellular tissues and maintaining the toughness of tissues. 90% of skin's dermis is consisting of collagen. Collagen gives skin its toughness, elasticity and moisture. It has been known that aging, ultraviolet (UV) radiation and the generation of free radicals all may destroy the structure among collagens, and thus, may cause degradation and loss of collagen, thereby accelerating the skin aging such as skin sagging and wrinkles.

Glycosylation is a chemical reaction in which glucose is attached to a protein and advanced glycation end products (AGEs) are thus generated. The AGEs accumulated in skin cells may not only lead to denaturation and loss of elasticity of protein those result in generation of skin wrinkles and skin aging, but also cause DNA damage and affect DNA's function in skin cells and even result in skin lesions.

Ultraviolet (UV) rays is also one of the primary factors that cause skin aging and skin lesions. It has been known that over 90% of UV in sunlight is UVA, which has very strong penetration to skin and can penetrate the dermis of skin and cause skin damages. Frequent exposure to UVA radiation will cause hyperactivation of matrix degrading enzymes, loss of collagen and elastin, acceleration of cell aging, and occurrence of aging phenomena (e.g., thickening of skin keratin, desiccation and desquamation of skin, generation of fine lines and dark spots, skin sagging, and loss of skin elasticity). In addition, UVA may also destroy the DNA of cells and cause DNA damage. Accumulation of excessive damaged DNA may not only cause cell aging but also lead to cellular variation, and thus, results in skin lesions and even skin cancer.

Therefore, an approach for resolving the above issues by using natural and safe materials is highly desirable in the art. Inventors of the present invention found that *Camellia sinensis* callus extract is effective in reducing the cell damage caused by UV, inhibiting loss of collagen in skin, promoting secretion of collagen in skin, inhibiting glycosylation of proteins in skin cells, and thus, can be used for nursing skin, repairing skin, improving skin condition, delaying skin aging, assisting in maintaining content of collagen in skin, against photodamage, preventing skin lesions, and/or promoting wound healing.

SUMMARY OF THE INVENTION

An objective of the present invention is to provide a use of a *Camellia sinensis* callus extract in the manufacture of a composition, wherein the extract is a polar solvent extract of calluses of *Camellia sinensis* leaves, and the composition is used for protecting skin. Preferably, the polar solvent is selected from a group consisting of water, C1-C4 alcohols, and combinations thereof. Preferably, the composition provided in accordance with the present invention is a care product composition, a food product composition, or a pharmaceutical composition.

Another objective of the present invention is to provide a composition, which is used for protecting skin. The composition is a care product composition, a food product composition, or a pharmaceutical composition and comprises an effective amount of a *Camellia sinensis* callus extract, wherein the extract is a polar solvent extract of calluses of *Camellia sinensis* leaves. Preferably, the polar solvent is selected from a group consisting of water, C1-C4 alcohols, and combinations thereof.

The care product composition provided in accordance with the present invention is used for at least one of nursing skin, repairing skin, improving skin condition, and delaying skin aging. Preferably, the care product composition is an essence, and the concentration of *Camellia sinensis* callus extract (as a dry matter) in the essence is from 0.01 to 10 wt %. Preferably, the care product composition is a lotion, and the concentration of *Camellia sinensis* callus extract (as a dry matter) in the lotion is from 0.01 to 5 wt %.

The food product composition provided in accordance with the present invention is used for assisting in maintaining content of collagen in skin. Preferably, the food product composition is a beauty beverage, and the concentration of *Camellia sinensis* callus extract (as a dry matter) in the beauty beverage is from 1 to 1000 ppm.

The pharmaceutical composition provided in accordance with the present invention is used for at least one of against photodamage, preventing skin lesions, and promoting wound healing. The pharmaceutical composition is provided as a form for transdermal administration, oral administration, or subcutaneous injection.

Still another objective of the present invention is to provide a method for protecting skin, comprising administering to a subject in need the composition as described above. The method in accordance with the present invention is for at least one of nursing skin, repairing skin, improving skin condition, delaying skin aging, assisting in maintaining content of collagen in skin, against photodamage, preventing skin lesions, and promoting wound healing.

The detailed technology and preferred embodiments implemented for the present invention are described in the following paragraphs accompanying the appended drawings for people skilled in this field to well appreciate the features of the claimed invention.

BRIEF DESCRIPTION OF THE DRAWINGS

The patent application contains at least one drawing executed in color. Copies of this patent with color drawing(s) will be provided by the Patent and Trademark Office upon request and payment of the necessary fee.

DESCRIPTION OF THE PREFERRED EMBODIMENTS

Figure 1:
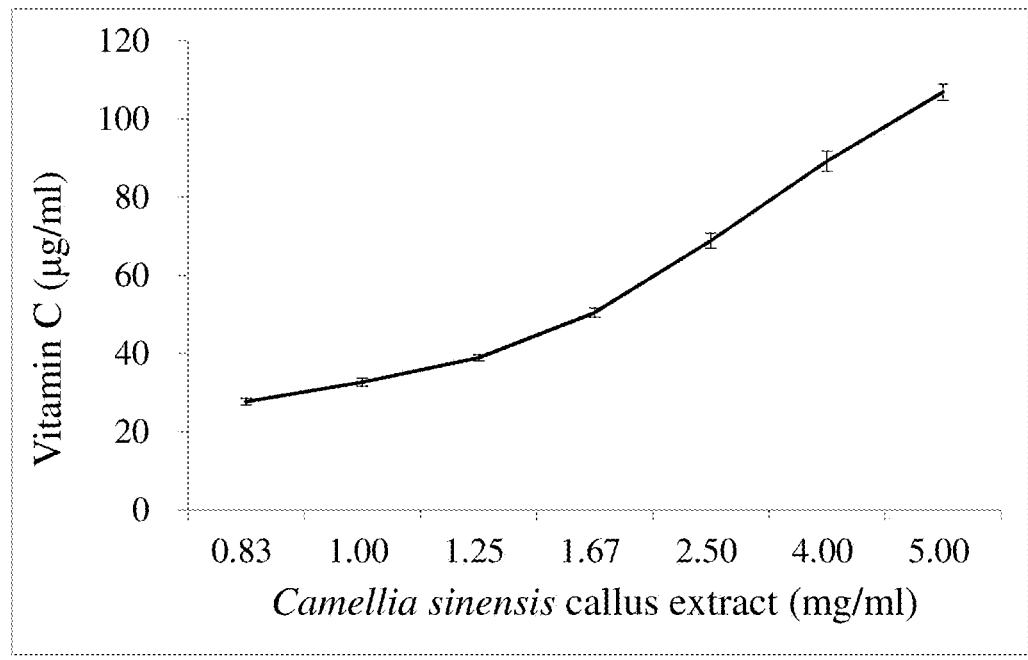
FIG. 1 shows the relationship between the concentration of vitamin C and that of *Camellia sinensis* callus extract for providing the same antioxidation effect, wherein the horizontal axis represents the concentration of *Camellia sinensis* callus extract, and vertical axis represents the concentration of vitamin C.

The following will describe some of the embodiments of the present invention in detail. However, without departing from the spirit of the present invention, the present invention may be embodied in various embodiments and should not be limited to the embodiments described in the specification. In addition, unless otherwise indicated herein, the expressions "a," "an," "the," or the like recited in the specification of the present invention (especially in the claims) are intended to include both the singular and plural forms. The term "subject" recited in this specification refers to a mammalian, including human and non-human animals. Furthermore, unless otherwise indicated herein, the term "*Camellia sinensis* callus" recited in this specification refers to the calluses of *Camellia sinensis* leaves.

Inventors of the present invention found that the features of calluses generated from the injured leaves of *Camellia sinensis* plant are similar to those of the pluripotent stem cells of mammals, and the extract of *Camellia sinensis* callus is effective in against UV damage, inhibiting glycosylation of proteins, promoting secretion of collagen, and delaying the degradation and loss of collagen.

Therefore, the present invention relates to the uses of a *Camellia sinensis* callus extract in protecting skin, including providing a composition comprising the *Camellia sinensis* callus extract, a use of the *Camellia sinensis* callus extract in the manufacture of a composition, and a method comprising administering a composition containing an effective amount of the *Camellia sinensis* callus extract to a subject in need so as to nurse skin, repair skin, improve skin condition, delay skin aging, assist in maintaining content of collagen in skin, against photodamage, prevent skin lesions, and/or promote wound healing. Particularly, the *Camellia sinensis* callus is the calluses of *Camellia sinensis* leaves.

The *Camellia sinensis* callus extract adopted in accordance with the present invention can be provided by extracting the calluses of *Camellia sinensis* leaves with a polar solvent, wherein the polar solvent can be a water, an alcohol (such as C1-C4 alcohols), or a combination thereof. Furthermore, there is no limitation of the amount of the extraction solvent as long as the materials can be evenly dispersed in the extraction solvent. For example, in the extraction step, the extraction solvent and *Camellia sinensis* callus could be used at a weight ratio ranging from 100:1 to 300:1 (extraction solvent: *Camellia sinensis* callus). Optionally, the extraction could be carried out accompanied with an ultrasonication to enhance the extraction efficiency. Preferably, a drying operation could be conducted prior to the extraction.

In some embodiments of the present invention, *Camellia sinensis* callus was freeze-dried prior to the extraction. For example, the freeze-dried *Camellia sinensis* callus could be mixed with water at a weight ratio of 100:1 (water:freeze-dried *Camellia sinensis* callus) to provide a mixture, and then the mixture was subjected to an ultrasonic agitation at 70° C. for 45 minutes to accomplish the extraction.

The *Camellia sinensis* callus adopted in accordance with the present invention could be provided by the following steps:
I. Washing *Camellia sinensis* plants with 2% sodium hypochlorite solution and then with sterile water, optionally, the aforementioned washing steps could be repeated;
II. Cutting the leaves of the washed *Camellia sinensis* plants to create wounds on their surfaces to induce the callus generation (for 1 to 3 months); and
III. Cultivating the callus(es) obtained from step II in a ½MS medium (½×Murashige and Skoog Basal Medium) at a temperature of 25° C. and a humidity of 50~60% (for 1 to 1.5 months).

The *Camellia sinensis* callus extract adopted in accordance with the present invention could be an original form of the liquid extract directly obtained from the extraction of *Camellia sinensis* callus, or a product obtained from carrying out one or more optional steps such as filtration, sterilization, concentration, and dilution on the liquid extract to facilitate the use of the liquid extract. For example, a powder product, which is convenient for carry or storage, could be provided by subjecting the liquid extract to an operation such as concentrating-drying, spray-drying, or freeze-drying.

The composition provided in accordance with the present invention could be a care product composition, a food product composition, or a pharmaceutical composition, wherein the care product composition could be used for at least one of nursing skin, repairing skin, improving skin condition, and delaying skin aging. The care product composition in accordance with the present invention could be provided in any suitable form without specific limitations. For example, the care product composition could be an emulsion, a cream, a gel (such as a hydrogel), or solution (such as an essence, a lotion), but is not limited thereby.

When the care product composition provided in accordance with the present invention is administered to the surface of skin for nursing skin, repairing skin, improving skin condition and/or delaying skin aging, the concentration of *Camellia sinensis* callus extract in the product could be varied depending on the type of the product. For example, when the care product composition is an essence, the concentration of *Camellia sinensis* callus extract (as a dry matter) in the essence is from 0.01 to 10 wt %, and preferably is 1 wt %. When the care product composition is a lotion, the concentration of *Camellia sinensis* callus extract (as a dry matter) in the lotion is from 0.01 to 5 wt %, and preferably is 0.1 wt %.

The food product composition provided in accordance with the present invention is used for assisting in maintaining content of collagen in skin, and could be provided in any suitable form without specific limitations. For example, the food product composition could be prepared as a form which is suitable for swallowing or drinking, such as a health beverage and a beauty beverage, but is not limited thereby. When the food product composition is a beauty beverage, the concentration of *Camellia sinensis* callus extract (as a dry matter) in the beauty beverage is from 1 to 1000 ppm, and preferably is 500 ppm.

Optionally, the care product composition, food product composition or pharmaceutical composition provided in accordance with the present invention could further comprise a suitable amount of additives, such as a flavoring agent, a toner, or a coloring agent for enhancing the palatability and the visual perception of the food product composition or pharmaceutical composition, and/or a buffer, a conservative, a preservative, an antibacterial agent, or an antifungal agent for improving the stability and storability of the care product composition, food product composition or pharmaceutical composition.

Depending on the desired purpose, the pharmaceutical composition in accordance with the present invention could be provided in any suitable form without specific limitations. For example, the pharmaceutical composition could be administered to a subject in need by an oral or parenteral (such as transdermal, or subcutaneous) route, but is not limited thereby. Depending on the form and purpose, suitable carriers can be chosen and used to provide the pharmaceutical composition, wherein the carriers include excipients, diluents, auxiliaries, stabilizers, absorbent retarders, disintegrating agent, hydrotropic agents, emulsifiers, antioxidants, adhesives, binders, tackifiers, dispersants, suspending agents, lubricants, hygroscopic agents, etc.

As a dosage form for oral administration, the pharmaceutical composition could comprise any pharmaceutically acceptable carriers that will not adversely affect the desired effects of the active ingredient (i.e., *Camellia sinensis* callus extract). Examples of suitable carriers include, but is not limited to, water, saline, dextrose, glycerol, ethanol or its analogs, cellulose, starch, sugar bentonite, and combinations thereof. The pharmaceutical composition could be provided in any suitable form for oral administration, such as in a form of a tablet (e.g., dragee), a pill, a capsule, granules, a pulvis, a fluid extract, a solution, syrup, a suspension, a tincture, etc.

As a dosage form for transdermal administration, the pharmaceutical composition could be provided in a form of such as a patch, an emulsion, a cream, a gel (such as a hydrogel), a paste (such as a dispersing paste, an ointment), a spray, or a solution (such as a suspension) for external use, but is not limited thereby.

As for the form of injections or drips suitable for subcutaneous administration, the pharmaceutical composition could comprise one or more ingredient(s), such as an isotonic solution, a salt-buffered saline (e.g., phosphate-buffered saline or citrate-buffered saline), a hydrotropic agent, an emulsifier, a 5% sugar solution, and other carriers. Alternatively, the pharmaceutical composition could be prepared as a pre-injection solid. The pre-injection solid could be provided in a form which is soluble in other solutions or suspensions, or in an emulsifiable form. A desired injection is provided by dissolving the pre-injection solid in other solutions or suspensions or emulsifying it prior to being administered to a subject in need.

Depending on the need, age, body weight, health conditions, and purpose of the subject, the composition provided in accordance with the present invention could be dosed at various administration frequencies, such as once a day, multiple times a day, once every few days, etc.

The present invention also provides a method for protecting skin, comprising administering to a subject in need a composition, wherein the composition comprises an effective amount of a *Camellia sinensis* callus extract. The applied type, applied route, applied form, applied frequency and uses in related application of the composition are all in line with the above descriptions.

The present invention will be further illustrated in detail with specific examples as follows. However, the following examples are provided only for illustrating the present invention and the scope of the present invention is not limited thereby. The scope of the present invention will be indicated in the appended claims.

EXAMPLES

Example 1

Preparation of *Camellia sinensis* Callus Extract

The *Camellia sinensis* plants were purchased from Guoguang Flower Market (Taichung, Taiwan) and were subjected to the following operations to provide *Camellia sinensis* callus(es):

I. Washing *Camellia sinensis* plants with 2% sodium hypochlorite solution then with sterile water, optionally, the aforementioned washing steps could be repeated;
II. Cutting leaves of the washed *Camellia sinensis* plants to create wounds on their surfaces to induce the callus generation (for 1 to 3 months); and
III. Cultivating the callus(es) obtained from step II in a ½MS medium (½×Murashige and Skoog Basal Medium, purchased from SIGMA company, product number: M5524) at a temperature of 25° C. and a humidity of 50~60% (for 1 to 1.5 months).

The *Camellia sinensis* calluses obtained from step III were subjected to the following operations to prepare a *Camellia sinensis* callus extract:

(1) Freeze-drying the *Camellia sinensis* calluses at −22° C. for 12 hours, then crushing the dried *Camellia sinensis* calluses to provide a *Camellia sinensis* callus powder;
(2) Mixing the *Camellia sinensis* callus powder obtained from step (1) with water at a weight ratio of water: *Camellia sinensis* callus powder=100:1 to provide a mixture, then subjecting the mixture to an ultrasonic agitation at 70° C. for 45 minutes;
(3) Filtrating the product of step (2) with a filter membrane to provide a filtrate;
(4) Heating the filtrate obtained from step (3) to 95° C. and maintaining at 95° C. for 20 minutes to sterilize;
(5) Cooling the product of step (4) (i.e., the primary liquid of *Camellia sinensis* callus extract for use in the following Examples), then packing and keeping the product in cold storage for use in the following experiments; and
(6) Freeze-drying the primary liquid of step (5) to provide a dry matter (i.e., *Camellia sinensis* callus extract adopted in accordance with the present invention).

Example 2

Effect of *Camellia sinensis* Callus Extract on Anti-Oxidation

The *Camellia sinensis* callus extract dry matter obtained from step (6) of Example 1 was divided into seven groups, and then independently mixed with reverse osmosis (RO) water to prepare seven solutions whose concentrations of *Camellia sinensis* callus extract were 0.83, 1.00, 1.25, 1.67, 2.50, 4.00 and 5.00 mg/ml respectively. Thereafter, each of the *Camellia sinensis* callus extract solutions was subjected to the following treatments respectively:
I. Mixing 2.5 ml of *Camellia sinensis* callus extract solution or 2.5 ml of standard with 2.5 ml of 0.2M phosphate-buffered saline (pH=6.6) and 2.5 ml of 1% potassium ferricyanide (PFC) to provide a mixed solution, and keeping the mixed solution at 50° C. for 20 minutes;
II. Cooling the product of step I, mixing the product with 2.5 ml of trichloroacetic acid (TCA) evenly to provide a mixture, and then, centrifuging the mixture at 3000 g for 10 minutes and collecting the supernatant; and
III. Mixing 3 ml of the supernatant obtained from step II with 3 ml of distilled water and 1.2 ml of 0.1% ferric chloride evenly to provide a mixed solution, then keeping the mixed solution at room temperature for 10 minutes, to provide a solution for use in the following absorbance measurement.

Vitamin C (purchased from SIGMA company) was divided into seven groups, and then independently mixed with water to prepare seven solutions whose concentrations of vitamin C were 0, 20, 40, 60, 80, 100 and 120 μg/ml respectively. Each of the seven vitamin C solutions was subjected to the treatments as described in above steps I to III, with the exception that the *Camellia sinensis* callus extract solution was replaced by the vitamin C solution.

Then, the absorbance value each of the solutions obtained from step III was measured by a spectrophotometer at the wavelength of 700 nm. A higher absorbance value represents a stronger reducing ability (i.e., a better antioxidant capability). Then, the absorbance value of *Camellia sinensis* callus extract solution was used as a basis to calculate the concentration of vitamin C that has an absorbance value identical to the corresponding *Camellia sinensis* callus extract solution. The results are shown in FIG. 1.

As shown in FIG. 1, the antioxidant capability of a 1 mg/ml *Camellia sinensis* callus extract solution is equivalent to that of a 30 μg/ml vitamin C solution. These results indicate that *Camellia sinensis* callus extract is excellent in antioxidation.

Example 3

Effects of *Camellia sinensis* Callus Extract on Against Photodamage (3-1) MTT Assay
Human skin fibroblasts (CCD-966SK; purchased from ATCC) were cultivated in a MEM medium (Minimum Essential Medium; purchased from Gibco, product number: 61100-061) for 24 hours. Thereafter, human skin fibroblasts were divided into seven groups and were independently subjected to the following treatments:
1. Control group: cells were cultivated in a MEM medium for 24 hours (i.e., the cells were cultivated in a medium free of *Camellia sinensis* callus extract).
2. "UVB" group: cells were cultivated in a MEM medium for 24 hours (i.e., the cells were cultivated in a medium free of *Camellia sinensis* callus extract), and then were irradiated with UVB (15 J/cm$^2$) for 1 hour.
3. "UVB+extract (0.375)" group, "UVB+extract (0.75)" group, "UVB+extract (1.5)" group, "UVB+extract (3)" group, and "UVB+extract (6)" group: cells of each group were cultivated in a MEM medium being externally added with the *Camellia sinensis* callus extract dry matter obtained from step (6) of Example 1 (to a final concentration of 0.375, 0.75, 1.5, 3 and 6 mg/ml, respectively) for 24 hours, and then were irradiated with UVB (15 J/cm$^2$) for 1 hour.

Figure 2:
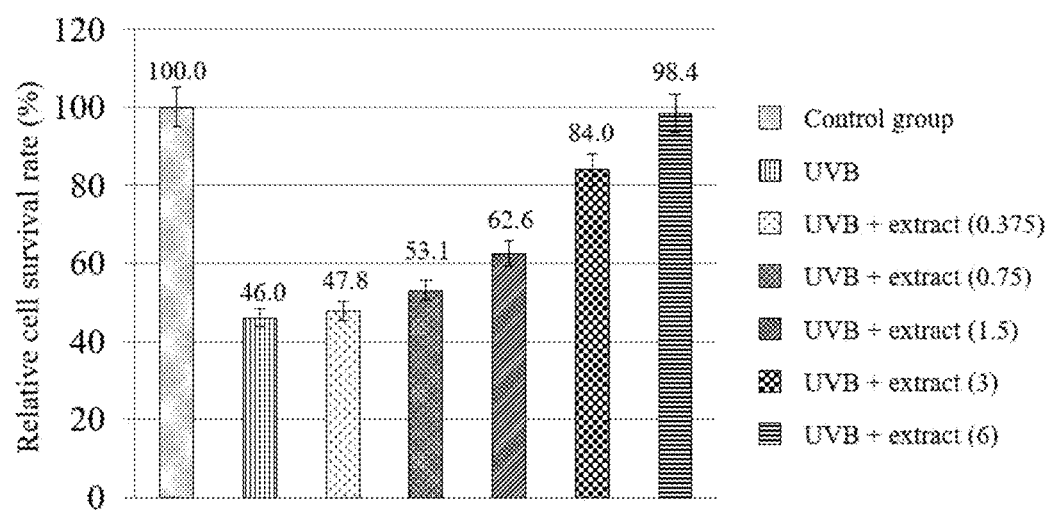
FIG. 2 shows, in comparison with the control group, the cell survival rate of each other group, wherein the human skin fibroblasts in control group were cultivated in a medium free of *Camellia sinensis* callus extract and were not irradiated with UVB, those in "UVB" group were cultivated in a medium free of *Camellia sinensis* callus extract but were irradiated with UVB, and those in "UVB+extract (0.375)" group, "UVB+extract (0.75)" group, "UVB+extract (1.5)" group, "UVB+extract (3)" group, and "UVB+extract (6)" group were irradiated with UVB and independently cultivated in a MEM medium being externally added with *Camellia sinensis* callus extract to a final concentration of 0.375, 0.75, 1.5, 3 and 6 mg/ml, respectively.

Thereafter, the cell survival rate of each group was determined by the MTT assay. The results are shown in FIG. 2. As shown in FIG. 2, in comparison with the control group, the cell survival rate of the "UVB" group was significantly lower. However, the cell survival rate of the groups treated with *Camellia sinensis* callus extract (including "UVB+extract (0.375)" group, "UVB+extract (0.75)" group, "UVB+extract (1.5)" group, "UVB+extract (3)" group, and "UVB+extract (6)" group) was significantly higher than that of the "UVB" group, and the concentration of *Camellia sinensis* callus extract was proportional to the cell survival rate.

(3-2) Fluorescent Staining
Human skin fibroblasts (CCD-966SK; purchased from ATCC) were cultivated in a MEM medium for 24 hours. Thereafter, the human skin fibroblasts were divided into three groups and were independently subjected to the following treatments:
1. Control group: cells were cultivated in a MEM medium for 24 hours (i.e., the cells were cultivated in a medium free of *Camellia sinensis* callus extract).
2. "UVA" group: cells were cultivated in a MEM medium for 24 hours (i.e., the cells were cultivated in a medium free of *Camellia sinensis* callus extract), and then were irradiated with UVA (15 J/cm$^2$) for 100 minutes.
3. "UVA+extract" group: cells were cultivated in a MEM medium being externally added with the *Camellia sinensis* callus extract dry matter obtained from step (6) of Example 1 to a final concentration of 5 mg/ml for 24 hours, and then were irradiated with UVA (15 J/cm$^2$) for 100 minutes.

Thereafter, the cells of each group were subjected to a fluorescent staining with Rhodamine 123 (i.e., a mitochondrial-specific dye; purchased from Thermo company) and Hoechest 33342 (i.e., a cell nuclear-specific dye; purchased from Thermo company), and then, the nuclei (shown as a blue fluorescence) and mitochondria (shown as a red fluorescence) in the cells of each group were observed by a fluorescence microscope. The results are shown in FIG. 3.

Figure 3:
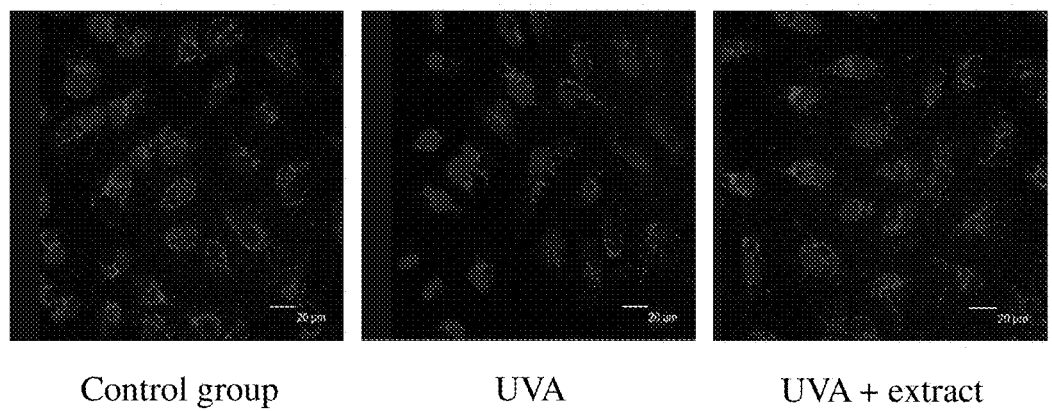
FIG. 3 shows, in comparison with the control group, the mitochondrial expression in cells of each other group, wherein the human skin fibroblasts in control group were cultivated in a medium free of *Camellia sinensis* callus extract and were not irradiated with UVA, those in "UVA" group were cultivated in a medium free of *Camellia sinensis* callus extract but were irradiated with UVA, and those in "UVA+extract" group were cultivated in a MEM medium being externally added with *Camellia sinensis* callus extract to a final concentration of 5 mg/ml and were irradiated with UVA.

As shown in FIG. 3, in comparison with the control group, the number of mitochondria in the cells of "UVA" group was significantly less. However, the number of mitochondria in the cells of "UVA+extract" group was almost equivalent to that of the control group.

The results of (3-1) and (3-2) indicate that *Camellia sinensis* callus extract can effectively reduce UVA- and UVB-induced damages to the cells and can be helpful for protecting mitochondria in human skin fibroblasts and repairing UV-induced damages to human skin fibroblasts. The results of (3-1) and (3-2) also indicate that the *Camellia sinensis* callus extract with an experimental concentration will not be toxic to normal human skin fibroblasts.

Example 4

Effect of *Camellia sinensis* Callus Extract on Inhibiting Protein Glycosylation To ascertain whether the *Camellia sinensis* callus extract provided in accordance with the present invention can inhibit protein glycosylation, the production level of advanced glycation end products (AGEs) was examined by the following experiments.

Experimental Groups:
(I) Respectively preparing a 60 mg/ml bovine serum albumin (BSA) solution (containing 0.06% sodium azide) and a 1.5M fructose solution by using 200 mM sodium phosphate buffer (pH=7.4) as a solvent;
(II) Subjecting the primary liquid of *Camellia sinensis* callus extract obtained from step (5) of Example 1 to a vacuum concentration to provide a 10-fold and a 100-fold concentrated liquid of *Camellia sinensis* callus extract respectively;
(III) Respectively mixing 0.25 ml each of the primary liquid of *Camellia sinensis* callus extract obtained from step (5) of Example 1, 10-fold concentrated liquid of *Camellia sinensis* callus extract obtained from step (II) and 100-fold concentrated liquid of *Camellia sinensis* callus extract obtained from step (II) with 0.25 ml BSA solution (containing 0.06% sodium azide) provided by step (I) and 0.25 ml fructose solution provided by step (I) evenly, and then, keeping the three mixed solutions thus obtained at 50° C. for 24 hours to provide three reaction solutions (hereinafter referred to as "primary liquid" group, "10-fold concentrated liquid" group and "100-fold concentrated liquid" group);
(IV) Measuring the fluorescence value of reaction solution of each group obtained from step (III) (0.1 ml reaction solution of each group was used) by using a fluorescence spectrometer at an excitation light wavelength of 360 nm and an emission light wavelength of 460 nm (i.e., 0-hr fluorescence value of each experimental group); and
(V) Incubating the reaction solution of each group obtained from step (III) at 50° C. for 24 hours (0.45 ml reaction solution of each group was used), and then, measuring fluorescence value of the incubated solution of each group (0.1 ml incubated solution of each group was used) by using a fluorescence spectrometer at an excitation light wavelength of 360 nm and an emission light wavelength of 460 nm (i.e., 24-hr fluorescence value of each experimental group).

Control Group:
(i) Preparing a 3 mM aminoguanidine (AG) solution by using 200 mM sodium phosphate buffer (pH=7.4) as a solvent;
(ii) Mixing 0.25 ml of AG solution provided by step (i) with 0.25 ml BSA solution (containing 0.06% sodium azide) provided by step (I) and 0.25 ml fructose solution provided by step (I) evenly, and then keeping the mixed solution at 50° C. for 24 hours to provide a reaction solution (hereinafter referred to as "control group");
(iii) Measuring the fluorescence value of the reaction solution obtained from step (ii) (0.1 ml reaction solution was used) by a fluorescence spectrometer at an excitation light wavelength of 360 nm and an emission light wavelength of 460 nm (i.e., 0-hr fluorescence value of the control group); and
(iv) Incubating the reaction solution obtained from step (ii) at 50° C. for 24 hours (0.45 ml reaction solution was used), and then measuring fluorescence value of the incubated solution (0.1 ml incubated solution was used) by a fluorescence spectrometer at an excitation light wavelength of 360 nm and an emission light wavelength of 460 nm (i.e., 24-hr the fluorescence value of the control group).

Thereafter, the relative production level of AGEs (%) of each experimental group was calculated by the following formula. The results are shown in FIG. 4.

$$\text{Relative production level of } AGEs\ (\%) = \left[ \frac{24\text{-}hr \text{ fluorescence of experimental group} - 0\text{-}hr \text{ fluorescence of experimental group}}{24\text{-}hr \text{ fluorescence of the control group} - 0\text{-}hr \text{ fluorescence of the control group}} \right] \times 100\%$$

Figure 4:
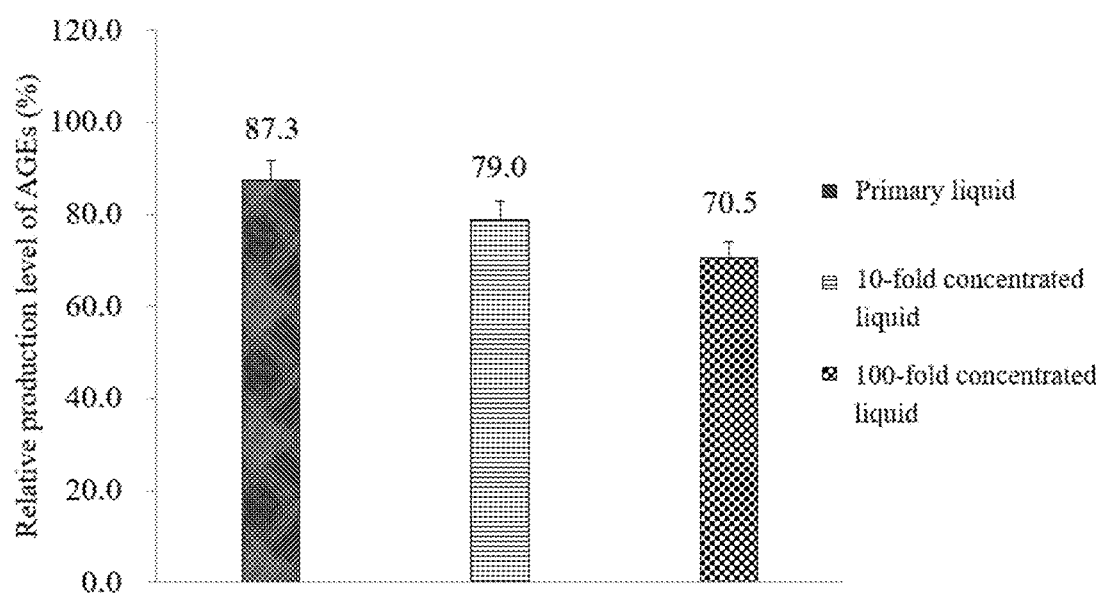
FIG. 4 shows the production level of AGEs (advanced glycation end products) in a reaction solution after the solution was treated by *Camellia sinensis* callus extract with different concentrations.

As shown in FIG. 4, *Camellia sinensis* callus extract can effectively inhibit AGEs production, and the concentrated liquids of *Camellia sinensis* callus extract exhibited a much significant effect. These results indicate that *Camellia sinensis* callus extract are effective in inhibiting the protein glycosylation, and thus, can be used for inhibiting glycosylation of proteins in human skin fibroblasts so as to achieve the effects of delaying skin aging and preventing skin lesions.

Example 5

Effects of *Camellia sinensis* Callus Extract on Assisting in Maintaining Content of Collagen in Skin (5-1) Promoting Secretion of Collagen To ascertain the effects of *Camellia sinensis* callus extract on promoting the secretion of collagen, human skin fibroblasts (CCD-966SK; purchased from ATCC) were cultivated in a MEM medium for 24 hours, and then, were divided into two groups and were independently subjected to the following treatments:
1. Control group: cells were cultivated in a MEM medium for 48 hours (i.e., the cells were cultivated in a medium free of *Camellia sinensis* callus extract).
2. "Extract" group: cells were cultivated in a MEM medium being externally added with the *Camellia sinensis* callus extract dry matter obtained from step (6) of Example 1 to a final concentration of 10 mg/ml for 48 hours.

Thereafter, the content of collagen in the culture medium of above two groups was examined by a Sircol™ Soluble Collagen Assay kit (purchased from Biocolor) and a ELISA reader (purchased from BioTek). Then, the data thus obtained was analyzed by Student's t-test, and the content of collagen in control group was used as a basis (i.e., the content of collagen of the control group was set as 100%) to calculate the relative content of collagen of "Extract" group. The results are shown in FIG. 5.

Figure 5:
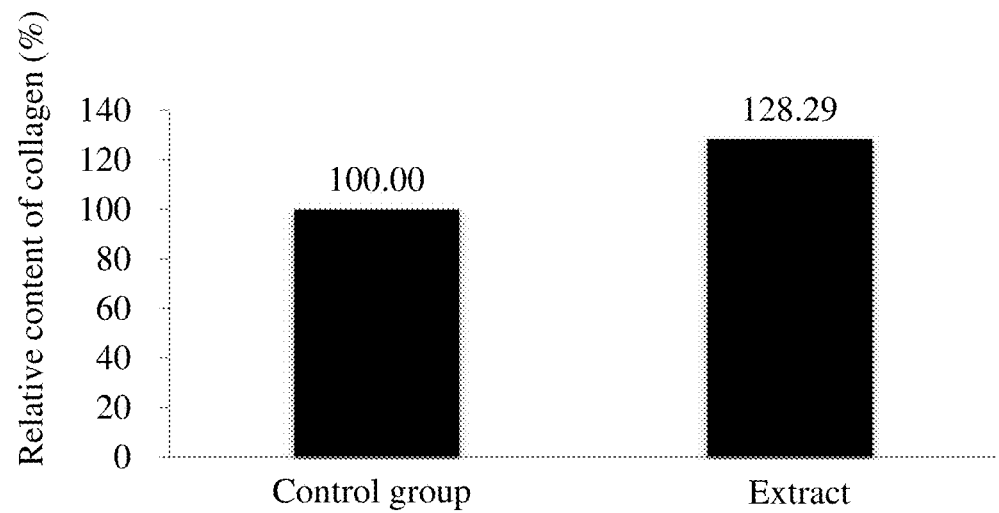
FIG. 5 shows, in comparison with the control group, the level of collagen secreted by the human skin fibroblasts in "Extract" group, wherein the human skin fibroblasts in control group were cultivated in a medium free of *Camellia sinensis* callus extract, and those in "Extract" group were cultivated in a MEM medium being externally added with *Camellia sinensis* callus extract to a final concentration of 10 mg/ml.

As shown in FIG. 5, in comparison with the control group, the content of collagen in "Extract" group was increased by 28.29%. The result indicates that *Camellia sinensis* callus extract can effectively promote cells to secret collagen, and thus, is effective in nursing skin, repairing skin, improving skin condition, delaying skin aging, and/or promoting wound healing.

(5-2) Delaying Loss of Collagen

It is known that, a decrement in expression level of MMP2 gene and/or an increment in expression level of TIMP1 gene can represent the collagen degradation is inhibited. To ascertain whether the *Camellia sinensis* callus extract provided in accordance with the present invention can delay degradation and loss of collagen in the skin, human skin fibroblasts (CCD-966SK; purchased from ATCC) were cultivated in a MEM medium for 24 hours, and then, were divided into three groups and were independently subjected to the following treatments:

1. Control group: cells were cultivated in a MEM medium for 6 hours (i.e., the cells were cultivated in a medium free of *Camellia sinensis* callus extract).
2. "Extract (0.125)" group: cells were cultivated in a MEM medium being externally added with the *Camellia sinensis* callus extract dry matter obtained from step (6) of Example 1 to a final concentration of 0.125 mg/ml for 6 hours.
3. "Extract (0.25)" group: cells were cultivated in a MEM medium being externally added with the *Camellia sinensis* callus extract dry matter obtained from step (6) of Example 1 to a final concentration of 0.25 mg/ml for 6 hours.

Thereafter the cells in each group were collected and subjected to qRT-PCR to determine the expression levels of MMP2 and TIMP1 genes in the cells of each group. Then, the data thus obtained was analyzed by Student's t-test, and the result of the control group was used as a basis (i.e., the expression level of the control group was set as 1-fold) to calculate the relative gene expression level of each other group. The results are shown in FIG. 6.

Figure 6:
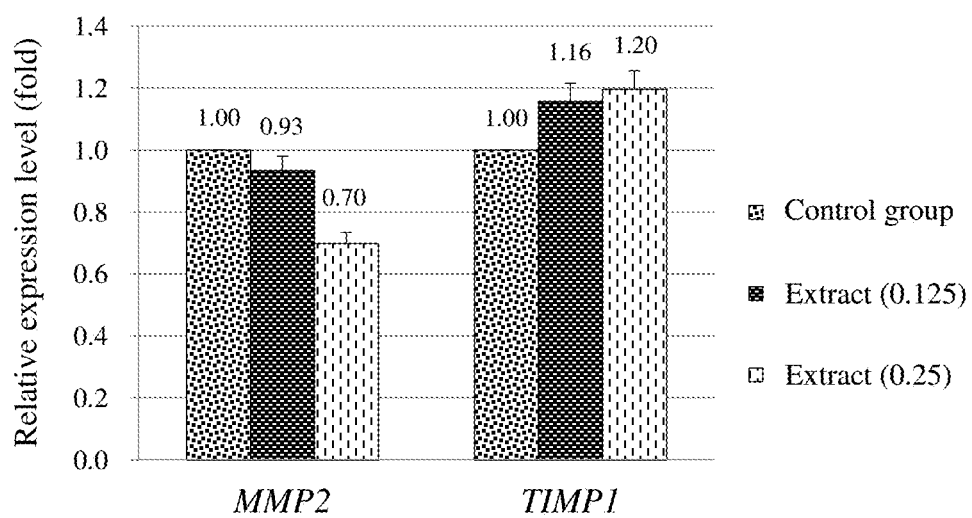
FIG. 6 shows, in comparison with the control group, the expression levels of MMP2 and TIMP1 genes in the human skin fibroblasts of each other group, wherein the human skin fibroblasts in control group were cultivated in a medium free of *Camellia sinensis* callus extract, and those in "Extract (0.125)" group and "Extract (0.25)" group were independently cultivated in a MEM medium being externally added with *Camellia sinensis* callus extract to a final concentration of 0.125 and 0.25 mg/ml respectively.

As shown in FIG. 6, in comparison with the control group, the expression level of MMP2 gene of the groups being treated by *Camellia sinensis* callus extract (including "Extract (0.125)" group and "Extract (0.25)" group) was significantly decreased, and the expression level of TIMP1 gene was significantly increased. These results indicate that *Camellia sinensis* callus extract can effectively inhibit degradation of collagen, and thus, can be used for delaying degradation and/or loss of collagen so as to achieve the effects of nursing skin, repairing skin, improving skin condition, delaying skin aging, and/or promoting wound healing.

As shown in the above Examples, *Camellia sinensis* callus extract provided in accordance with the present invention can indeed inhibit glycosylation of proteins in skin cells, promote skin cells to secret collagen, inhibit degradation of collagen, delay loss of collagen, and increase survival rate of skin cells under a UV light irradiation, and thus, is effective in protecting skin such as nursing skin, repairing skin, improving skin condition, delaying skin aging, assisting in maintaining content of collagen in skin, against photodamage, preventing skin lesions, and/or promoting wound healing.

What is claimed is:

1. A method for treating skin aging and photodamage, comprising administering to a subject in need thereof, a composition, wherein the composition consists of (i) an effective amount of a *Camellia sinensis* callus extract; and (ii) at least one of a buffer, a preservative, and antibacterial agent, and an antifungal agent, wherein the extract is a polar solvent extract of calluses of *Camellia sinensis* leaves, and the calluses are obtained by cutting leaves of *Camellia sinensis* to induce a callus generation.

2. The method as claimed in claim 1, wherein the polar solvent is selected from a group consisting of water, C1-C4 alcohols, and combinations thereof.

3. The method as claimed in claim 1, wherein the composition is a pharmaceutical composition.

4. The method as claimed in claim 1, wherein the composition is administered to the subject to treat skin aging.

5. The method as claimed in claim 1, wherein the composition is administered to the subject to assist in maintaining content of collagen.

6. The method as claimed in claim 1, wherein the composition is a pharmaceutical composition and is administered to the subject to treat photodamage.

7. The method as claimed in claim 6, wherein the pharmaceutical composition is administered to the subject by transdermal administration, oral administration, subcutaneous injection, or a combination thereof.

8. The method as claimed in claim 2, wherein the composition is a pharmaceutical composition.

9. The method as claimed in claim 2, wherein the composition is administered to the subject to treat skin aging.

10. The method as claimed in claim 2, wherein the composition is administered to the subject to assist in maintaining content of collagen.

11. The method as claimed in claim 2, wherein the composition is a pharmaceutical composition and is administered to the subject to treat photodamage.

12. The method as claimed in claim 11, wherein the pharmaceutical composition is administered to the subject by transdermal administration, oral administration, subcutaneous injection, or a combination thereof.

* * * * *